US011491013B2

(12) United States Patent
Servidio

(10) Patent No.: US 11,491,013 B2
(45) Date of Patent: Nov. 8, 2022

(54) AUGMENT AND MEANS FOR CONNECTING THE SAME TO A JOINT PROSTHESIS

(71) Applicant: Howmedica Osteonics Corp., Mahwah, NJ (US)

(72) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 21 days.

(21) Appl. No.: 16/924,841

(22) Filed: Jul. 9, 2020

(65) Prior Publication Data

US 2021/0007851 A1 Jan. 14, 2021

Related U.S. Application Data

(60) Provisional application No. 62/872,843, filed on Jul. 11, 2019.

(51) Int. Cl.
*A61F 2/30* (2006.01)
*A61F 2/38* (2006.01)

(52) U.S. Cl.
CPC ........ *A61F 2/30734* (2013.01); *A61F 2/3859* (2013.01); *A61F 2002/30433* (2013.01); *A61F 2002/30736* (2013.01)

(58) Field of Classification Search
None
See application file for complete search history.

(56) References Cited

U.S. PATENT DOCUMENTS

| 4,936,847 | A | | 6/1990 | Manginelli |
| 4,950,298 | A | | 8/1990 | Gustilo et al. |
| 5,370,693 | A | | 12/1994 | Kelman et al. |
| 5,387,241 | A | | 2/1995 | Hayes |
| 5,458,637 | A | | 10/1995 | Hayes |
| 5,549,685 | A | * | 8/1996 | Hayes ............... A61F 2/3859 623/20.16 |
| 5,571,194 | A | | 11/1996 | Gabriel |
| 5,609,645 | A | * | 3/1997 | Vinciguerra ........ A61F 2/3859 623/20.28 |
| 5,755,800 | A | | 5/1998 | O'Neil et al. |
| 5,766,255 | A | * | 6/1998 | Slamin ............... A61F 2/3859 623/20.15 |

(Continued)

FOREIGN PATENT DOCUMENTS

WO 0023010 A1 4/2000

Primary Examiner — Ann Schillinger
(74) Attorney, Agent, or Firm — Lerner, David, Littenberg, Krumholz & Mentlik, LLP

(57) ABSTRACT

An orthopedic system includes an augment that includes a proximal surface and a distal surface, a recessed slot extending along the distal surface, and a through-bore extending between the proximal and distal surfaces and intersecting the slot. The system also includes a coupling component that includes a head and a body. The head has an aperture and is configured to be slidingly received by the recessed slot wherein, when the head is received within the recessed slot, the aperture aligns with the through-bore. The system further includes a femoral prosthesis that has an articular side that defines condylar portions and a bone facing side opposite the articular side. The bone facing side defines a coupling bore. The coupling bore is configured to receive the body of the coupling component for connection thereto.

20 Claims, 5 Drawing Sheets

(56) References Cited

U.S. PATENT DOCUMENTS

| | | | |
|---|---|---|---|
| 5,879,393 A * | 3/1999 | Whiteside | A61B 17/155 606/88 |
| 5,984,969 A * | 11/1999 | Matthews | A61F 2/3859 623/20.11 |
| 6,005,018 A * | 12/1999 | Cicierega | A61F 2/30734 623/20.16 |
| 6,074,424 A * | 6/2000 | Perrone, Jr. | A61F 2/3859 623/20.3 |
| 6,896,702 B2 | 5/2005 | Collazo | |
| 8,187,280 B2 | 5/2012 | May et al. | |
| 8,632,599 B1 | 1/2014 | Bonitati et al. | |
| 8,702,460 B2 | 4/2014 | Szydlowski et al. | |
| 9,162,008 B2 | 10/2015 | Serafin, Jr. et al. | |
| 9,320,603 B2 | 4/2016 | Lieberman et al. | |
| 9,408,699 B2 | 8/2016 | Stalcup et al. | |
| 9,532,879 B2 | 1/2017 | Lieberman et al. | |
| 2011/0015751 A1 | 1/2011 | Laird | |
| 2013/0013077 A1* | 1/2013 | Metzger | A61F 2/3859 623/20.35 |
| 2014/0005791 A1* | 1/2014 | Bonitati | A61F 2/30734 623/20.15 |
| 2014/0358242 A1 | 12/2014 | Mines | |
| 2015/0335438 A1 | 11/2015 | Pierce et al. | |

\* cited by examiner

AUGMENT AND MEANS FOR CONNECTING THE SAME TO A JOINT PROSTHESIS

CROSS-REFERENCE TO RELATED APPLICATIONS

This application claims the benefit of the filing date of U.S. Provisional Patent Application No. 62/872,843, filed Jul. 11, 2019, the disclosure of which is hereby incorporated herein by reference.

BACKGROUND OF THE INVENTION

The knee joint consists generally of three distinct regions, the medial tibiofemoral compartment, the lateral tibiofemoral compartment and the patellofemoral compartment. Any one of these compartments or combination of compartments can become damaged or diseased. For example, osteoarthritis can destroy articular cartilage within the tibiofemoral and/or patellofemoral joints producing painful bone-on-bone articulation and malalignment of the knee.

Knee replacement surgery can be tailored to treat the specific condition diagnosed. For example, for patients with isolated compartmental disease, a partial knee replacement or partial knee arthroplasty (""PKA"") procedure may be performed, such as unicompartmental knee replacement or patellofemoral joint replacement. In patients with arthritis in all three compartments, a total joint knee replacement or total knee arthroplasty (""TKA"") may be performed.

Patients who undergo primary knee replacement surgery, whether for a PKA or a TKA, can expect to undergo one or more revision procedures. The causes for revision surgery can vary from mechanical failure of the implant, infection of the joint, aseptic loosening of the implant, or joint instability due to the progression of disease. Continued arthritic changes of the joint over time often results in changes to the quality of the bone as well as deterioration of the strength and efficacy of the ligamentous structures.

Amongst the many drawbacks associated with revision knee surgery is the loss of bone associated with the explantation of the prior components which may be compounded by underlying disease. Thus, significant condylar defects oftentimes present themselves upon explantation. When such condylar defect is present, the surgeon may correct this condition by preparing the defective bone to accept a joint implant that includes an augment. For example, a distal end of a femur may be resected to remove the defect or diseased bone which may be more significant on one condyle relative to the other, thus resulting in one resected condylar surface being distally offset relative to the other. To ensure establishment of the desired joint line and sufficient anchoring and proper fit of the femoral component, an augment is connected to a bone facing side of the femoral component so as to fill in the space or spaces between the femoral component and the resected surface(s). In this regard, augments are typically used with a joint prosthesis to increase the thickness of the joint prosthesis at designated locations thereof in order to compensate for lack of sufficient bone tissue.

Current augments can be connected to an associated joint prosthesis using a variety of means. However, such means currently available may be limited by the geometry of the augment and/or the associated joint prosthesis. Accordingly, such means may be either too time consuming to manipulate resulting in extended procedure times or do not sufficiently connect to the joint prosthesis. Thus, further improvements are desirable.

BRIEF SUMMARY OF THE INVENTION

In one aspect of the present disclosure, an orthopedic system includes an augment that includes a proximal surface and a distal surface, a recessed slot extending along the distal surface, and a through-bore extending between the proximal and distal surfaces and intersecting the slot. The system also includes a coupling component that includes a head and a body. The head has an aperture and is configured to be slidingly received by the recessed slot wherein, when the head is received within the recessed slot, the aperture aligns with the through-bore. The system further includes a femoral prosthesis that has an articular side that defines condylar portions and a bone facing side opposite the articular side. The bone facing side defines a coupling bore. The coupling bore is configured to receive the body of the coupling component for connection thereto.

In another aspect of the present disclosure, an orthopedic system includes an augment that has a proximal end and a distal end and a through-bore extending between the proximal end and the distal end. The through-bore is configured for insertion of a tool. The system also includes a fastener that has a head and a body. The head has an aperture. The fastener is rotatably connected to the distal end of the augment such that the aperture aligns with the through-bore, and the entirety of the through-bore extends between the head and the proximal end of the augment. The system further includes a femoral prosthesis that has an articular side that defines condylar portions and a bone-facing side opposite the articular side. The bone-facing side defines an inner surface. The inner surface has a bore configured to receive the body of the fastener such that, when the body of the fastener is received within the bore of the femoral prosthesis, the distal surface of the augment contacts the inner surface of the femoral prosthesis and the head of the fastener is captured between the femoral prosthesis and the augment.

In a further aspect of the present disclosure, an orthopedic system includes an augment that has a bone facing surface and an implant facing surface. The augment defines a through-bore that extends through the bone facing surface. The through-bore is configured for insertion of a tool. The system also includes a fastener that has a head and a body and is rotatably connected to the augment such that the through-bore extends between the head and bone facing surface. The head has a cross-sectional dimension greater than that of the through-bore. The system further includes a femoral implant that has an articular side that defines condylar portions and a bone-facing side opposite the articular side. The bone-facing side has an inner surface and a bore extending through the inner surfaces such that, when the body of the fastener extends into the bore of the femoral implant, the implant facing surface contacts the inner surface of the femoral implant and the head is positioned between the through-bore and the inner surface of the implant.

DETAILED DESCRIPTION OF THE INVENTION

When referring to specific directions in the following discussion of certain implantable joint replacement devices, it should be understood that such directions are described with regard to the orientation and position of the implantable joint replacement devices during exemplary application to the human body. Thus, as used herein, the term "proximal" means closer to the heart and the term "distal" means further from the heart. The term "anterior" means toward the front part of the body or the face, and the term "posterior" means toward the back of the body. The term "medial" means toward the midline of the body, and the term "lateral" means away from the midline of the body. The term "inferior" means toward the feet of the body, and the term "superior" means toward the head of the body. Further, as used herein, the terms "about," "generally," and "substantially" are intended to mean deviations from absolute are included within the scope of the term so modified.

Figure 1:
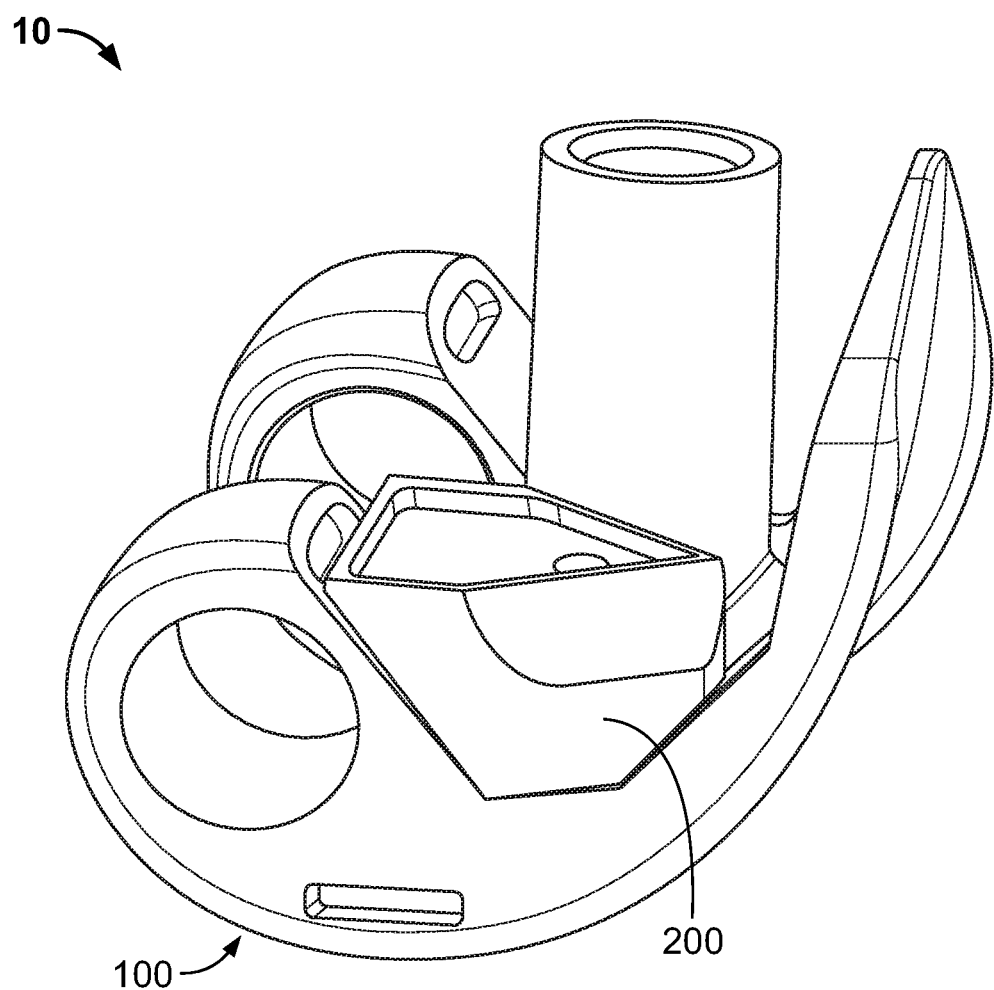
FIG. 1 is a perspective view of a joint replacement system including a femoral component and an augment and according to one embodiment of the present disclosure.

Referring to FIG. 1, a system 10 for a joint replacement is shown. System 10 comprises a femoral component 100, an augment 200, and a fastener 300 (see FIG. 4). The constituent parts of system 10 are described in more detail below.

Figure 2A:
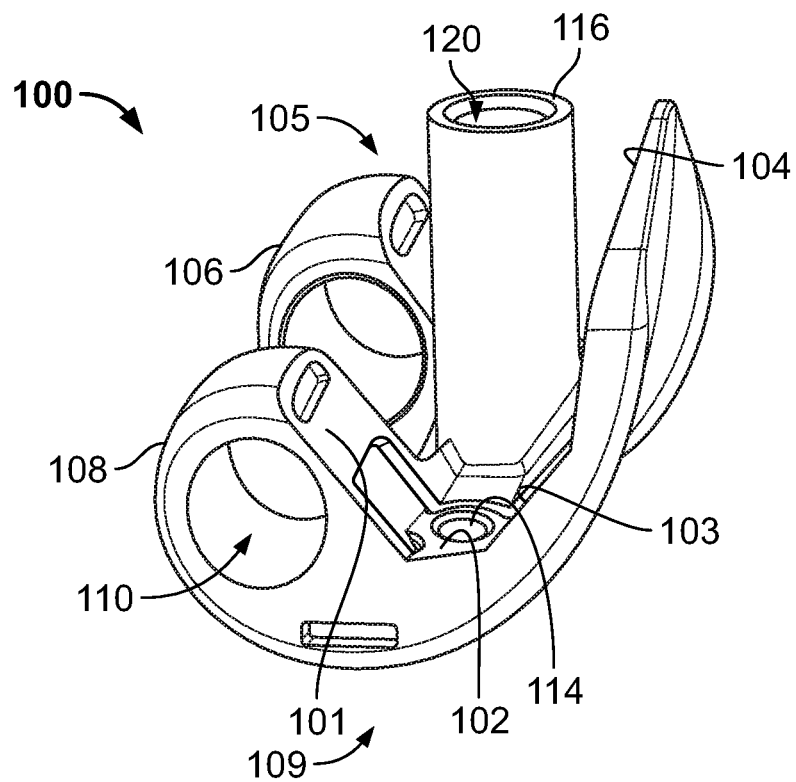
FIG. 2A is a perspective view of the femoral component of FIG. 1."
Figure 2B:
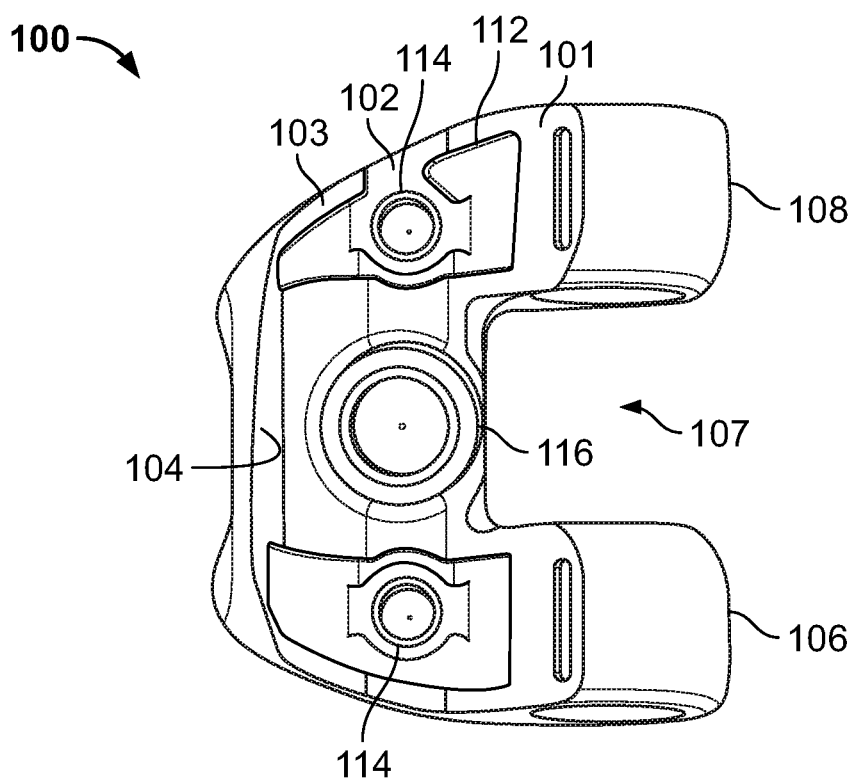
FIG. 2B is a top view of the femoral component of FIG. 2A.

FIGS. 2A and 2B illustrate femoral component 100. Femoral component 100 is a hinge knee femoral component particularly adapted for a hinge TKA prosthesis. However, femoral component 100 may be adapted for any type of TKA prosthesis. For example, femoral component 100 may be a cruciate retaining, posterior stabilized, or total stabilized femoral component, as are known in the art.

Femoral component 100 generally includes a bone facing side 102, an articular side 109, and lateral and medial condylar portions 106, 108. Condylar portions 106 and 108 are separated by an intercondylar recess or notch 107 at a posterior aspect of femoral component 100, as best shown in FIG. 2B. A transverse opening 110 extends through condylar portions 106, 108 between bone facing and articular sides 105, 109 and at a posterior aspect of femoral component 100. Transverse opening 110 is intersected by intercondylar recess 107 and is configured to receive an axle (not shown) about which a tibia flexes and extends. Such axle and other prosthetic hinge knee components that may be utilized in conjunction with femoral component 100 can be found in U.S. Publication No. 2017/0035572, the disclosure of which is hereby incorporated herein by reference in its entirety.

The bone facing side 105 includes a plurality of intersecting inner bone facing surfaces 101-104 which each correspond to a resected surface of a distal femur. The plurality of intersecting bone facing surfaces 101-104 are generally planar surfaces. However, while such surfaces 101-104 are generally planar, they can include depressions, such as depression 112 shown in FIG. 2B, and the like for receipt of bone cement, for example. However, their respective profiles are each as a planar surface to match a corresponding planar resected surface of a femur. In the embodiment depicted, femoral component 100 includes four bone facing surfaces 101-104 that correspond to four resected surfaces of a femur. Femoral component 100 may, however, have five of such inner surfaces, although femoral component 100 preferably includes four inner bone facing surfaces 101-104 in order to accommodate transverse opening 110. In other embodiments, bone facing side 105 may have only three bone facing surfaces which would also accommodate transverse opening 110. However, four inner bone facing surfaces is preferred over three because it allows for less bone removal than three inner surfaces while providing for sufficient thickness at the posterior aspect of femoral component 100 for transverse opening 110.

Bores 114 extend into inner surface 102 at lateral and medial sides of femoral component 100, as best shown in FIG. 2B. Bores 114, in the particular embodiment depicted, are threaded blind holes which are dimensioned to each receive a threaded body of fastener 300, as described in more detail below. However, in some embodiments, bores 114 may be tapered for a taper-lock connection or may be configured for a snap-fit connection, for example. Although bores 114 are shown as extending into inner surface 102, one or more bores 114 may also extend into any one of surfaces 101, 103, and 104 so that another similarly configured augment can be connected to such surfaces as well.

Figure 3A:
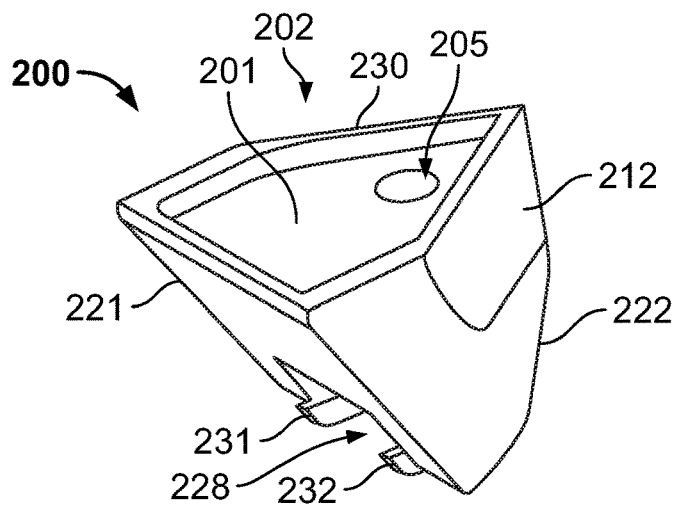
FIG. 3A is a perspective view of the augment of FIG. 1.
Figure 3B:
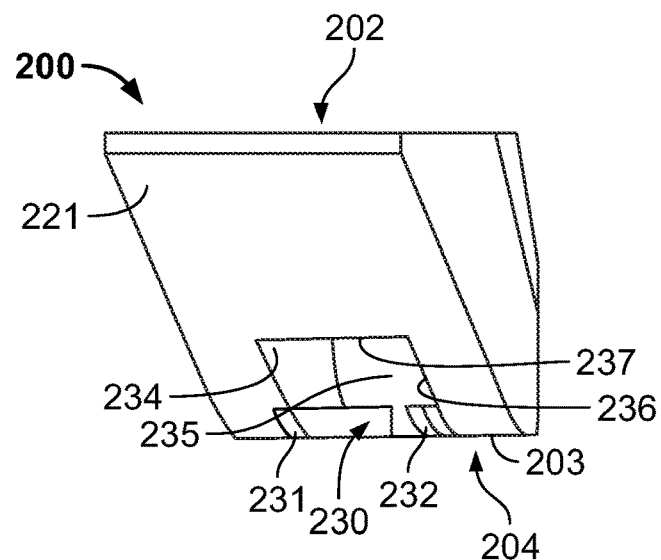
FIG. 3B is another perspective view of the augment of FIG. 3A.
Figure 3C:
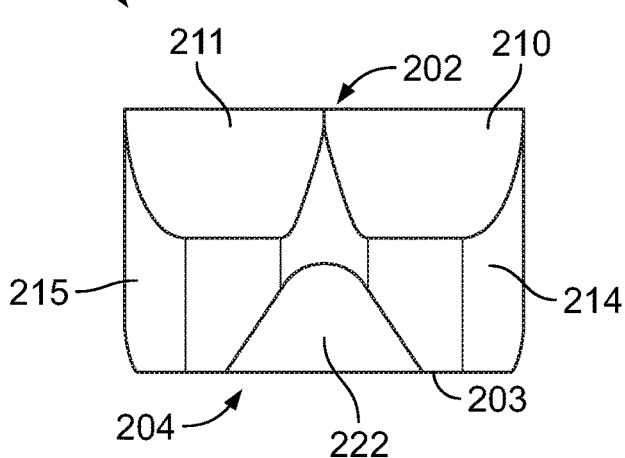
FIG. 3C is a front elevational view of the augment of FIG. 3A.

Referring to FIGS. 3A-C, augment 200 is shown. Augment 200 has a proximal end 202 and a distal end 204. When connected to femoral component 100, proximal end 202 faces the same direction as the bone facing side 102 of femoral component 100. In this regard, proximal end 202 of augment 200 is a bone facing side of augment 200. Proximal end 202 has a planar proximal surface 201 surrounded by a lip or rim 230 extending along the entirety of its perimeter. Thus, proximal surface 201 is recessed within proximal end 202 of augment 200 so that bone cement can be deposited within rim 230 and atop of proximal surface 201. In some embodiments in which no bone cement is utilized, augment 200 may not include a lip 230 surrounding surface 201. Distal end 204 faces the opposite direction as proximal end 202 and, therefore, is an implant facing side of augment 200 as distal end 204 faces femoral component 100 when connected thereto. Augment 200 also includes a plurality of side surfaces that extend between proximal and distal ends 202, 204. In the embodiment depicted, such surfaces include first and second chamfer surfaces 221 and 222 and side surfaces 210-215. First and second chamfer surfaces 221 and 222 intersect distal surface 203 at an oblique angle. Distal surface 203 is configured to correspond with second inner surface 102 of femoral component, while first and second chamfer surfaces 221, 222 are configured to correspond to and respectively contact first and third inner contact surfaces 101, 103 of femoral component 100 when connected thereto. As best seen in FIG. 1, the profiles of distal surface 203 and chamfer surfaces 221 and 222 allow placement flush on bone facing side 105 of femoral component 100. Side surfaces 210-211 intersect each other to form a general boat-shaped structure.

A recessed slot 230 extends through first chamfered surface 221 and distal surface 203, as best shown in FIG. 3B. Slot 230 is defined by opposing flanges or rails 231, 232 and by a lateral walls 234 and 236, proximal wall 237 and anterior wall 235. Recessed slot 230 and flanges 231, 232 extend in an anteroposterior direction and each terminate at anterior wall 235. Lateral walls 234 and 236 are positioned proximal of flanges 231 and 232, respectively, and are separated from each other by a distance greater than a distance separating flanges 231 and 232. In this regard, slot 230 has a first section defined between lateral walls 234 and 236 that has a greater cross-sectional dimension than a second section defined between flanges 231 and 232. In this regard, recessed slot 206 is configured to slidingly receive fastener 300 such that a head thereof can be received within the first section but not in the second section between flanges 231 and 232. Anterior wall 235 acts as a depth-stop for such fastener 300. Although recessed slot 230 is described as extending in an anteroposterior direction through first chamfered surfaced 221, it is contemplated that in other embodiments such recessed slot 230 may be configured to extend laterally-medially through surfaces 212 or 213, for example.

Augment 200 also includes a through-bore 205, the entire length of which extends between proximal end 202 and distal end 204. More particularly, through-bore 205 extends through proximal surface 201 and proximal wall 237 such that through-bore intersects recessed slot 230. Through-bore 205 has a cross-sectional dimension smaller than that of a head of fastener 300, as described in more detail below.

Augment 200, as shown, is monolithic, and, therefore, its constituent parts may be formed together as a single, integral structure. In addition, augment 200 may include porous surfaces, such as along surfaces that are bone contacting in order to promote bone ingrowth. Augment 200 can be made via an additive layer manufacturing ("ALM") process. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901 as well as U.S. Patent Publication No. 2006/0147332, each of which is hereby incorporated by reference in their entireties herein. Other methods of ALM, which can be used to form augment 200, include stereolithography (SLA), fused deposition modeling (FDM), and continuous liquid interface production (CLIP).

Figure 4:
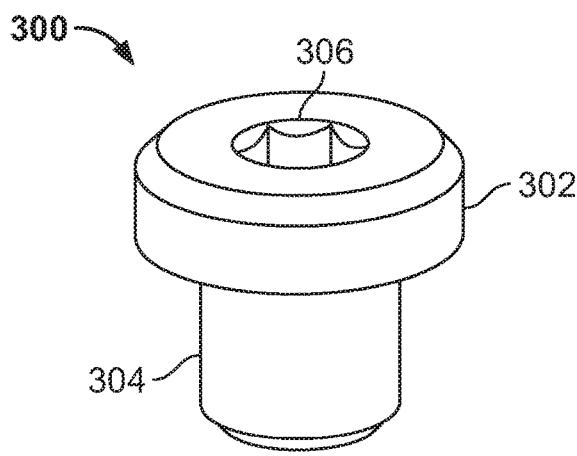
FIG. 4 is a perspective view of a fastener according to one embodiment of the present disclosure.

Referring to FIG. 4, fastener 300 is shown. Fastener 300 includes a head 302, body 304, and aperture 306 extending into head 302. Fastener 300 is a threaded fastener. In this regard, body 304 is a threaded shaft. However, in some embodiments, body 304 can be a tapered shaft for a taper-lock connection with femoral component 100, or may have a projection extending therefrom for a snap-fit connection, for example.

Figure 5A:
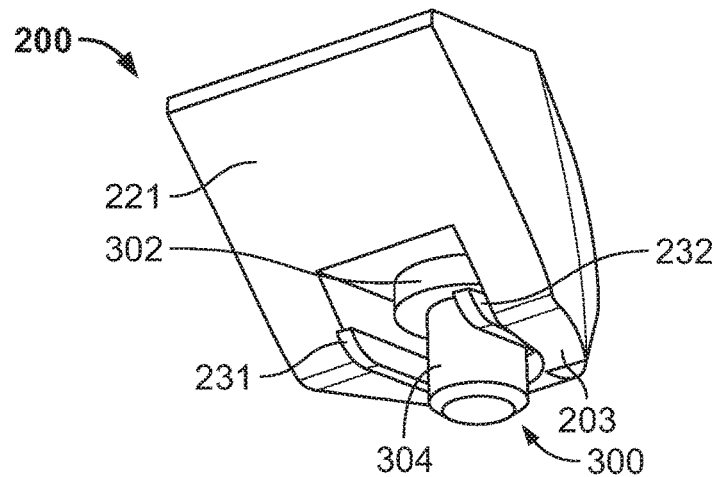
FIG. 5A is a perspective view of an assembly that includes the fastener of FIG. 4 the augment of FIG. 3A.
Figure 5B:
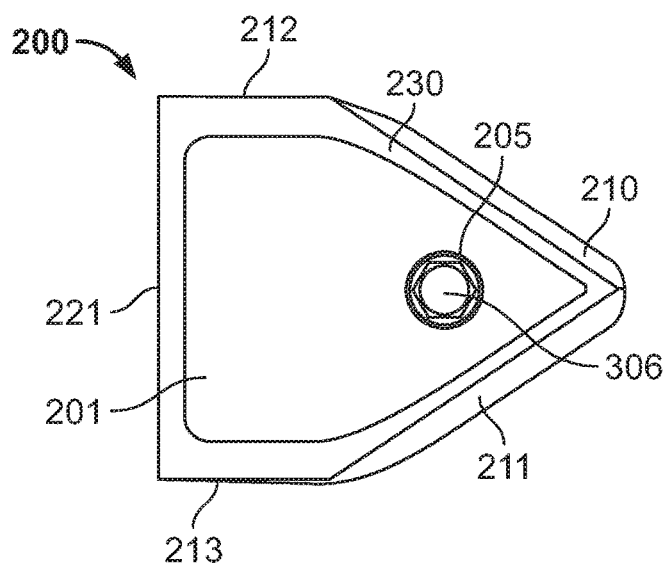
FIG. 5B is a top view of the assembly of FIG. 5A.

FIGS. 5A and 5B illustrate the connection between augment 200 and fastener 300. Head 302 is slidably received within recessed slot 230 and fits within recessed slot 206 proximal to flanges 231 and 232 in such a way that it rests on such flanges 231, 232. Flanges 231, 232 prohibit axial movement of fastener 300 when it is received in recessed slot 230. However, fastener 300, when received within slot 230, is rotatable therein. Anterior wall 235 provides an abutment that prohibits movement of the head 302 beyond a predefined location in the anterior direction. Such predefined location is such that when head 302 abuts anterior wall 235, aperture 306 is coaxially aligned with through-bore 205, as best shown in FIG. 5B. This allows a driver tool (not shown) to be passed through through-bore 205 and engage aperture 306 so that fastener 300 can be rotated.

Figure 5C:
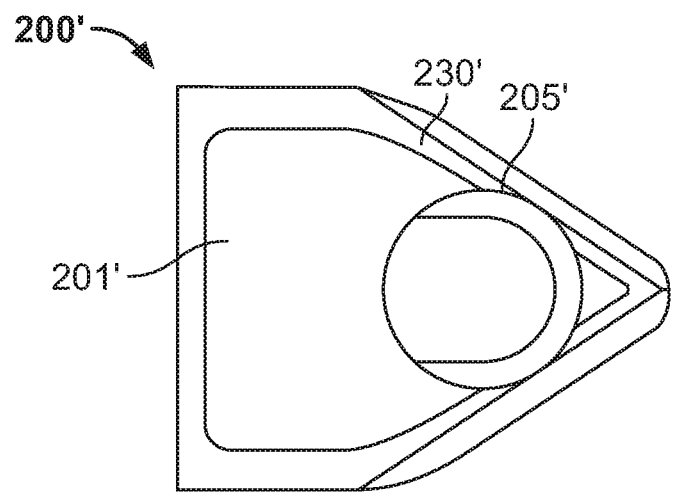
FIG. 5C is a top view of an augment according to another embodiment of the present disclosure.

As mentioned above, through-bore 205 has a smaller cross-sectional dimension than head 302. This allows for through-bore 205 to occupy minimal area at the proximal end of augment 200. This is best shown by contrasting augment 200, as depicted in FIG. 5B, with an alternative augment 200', as depicted in FIG. 5C. Augment 200' has a through-bore 205' that has a cross-sectional dimension slightly larger than head 302 so that fastener 300 can be loaded through a proximal end of augment 200' and so that head 302 can be recessed below a proximal surface 201' thereof. However, as shown, through-bore 205' occupies a significant amount of area at the proximal end of augment 200' as well as volume extending into augment 200'. Moreover, through-bore 205' intersects a rim 230' surrounding surface 201' which may undesirably result in cement being uncontained by rim 230'. In this regard, such an embodiment can compromise strength of augment 200' and fixation between augment 200' and bone. In contrast, through-bore 205 occupies a comparatively smaller area at proximal surface 201 and a small volume extending through augment 200.

Fastener 300 can be side-loaded into augment 200 which is facilitated by the recessed slot 230 and the flanges 231, 232 which engage head 302, as best seen in FIG. 5A. Once fastener 300 is loaded into augment 200, it is ready to be connected to femoral component 100. This is achieved by first mounting augment 200 onto bone facing side 105 of femoral component 100 and so that body 304 engages a respective bore 114. Augment 200 can be mounted onto the lateral or medial side of femoral component 100 depending on where the distal femur requires augmentation. In this regard, one or two augments 200 may be connected to femoral component 100. Once body 304 is received in a respective bore 114 of femoral component 100, a driver tool may be inserted through through-bore 205 and into engagement with aperture 205 of fastener 300. The driver tool can then be used to drive body 304 into bore 114 which causes head 302 to press distal surface 203 against second surface 102 and chamfer surfaces 221 and 222 firmly against surfaces 101 and 103, respectively.

Figure 6:
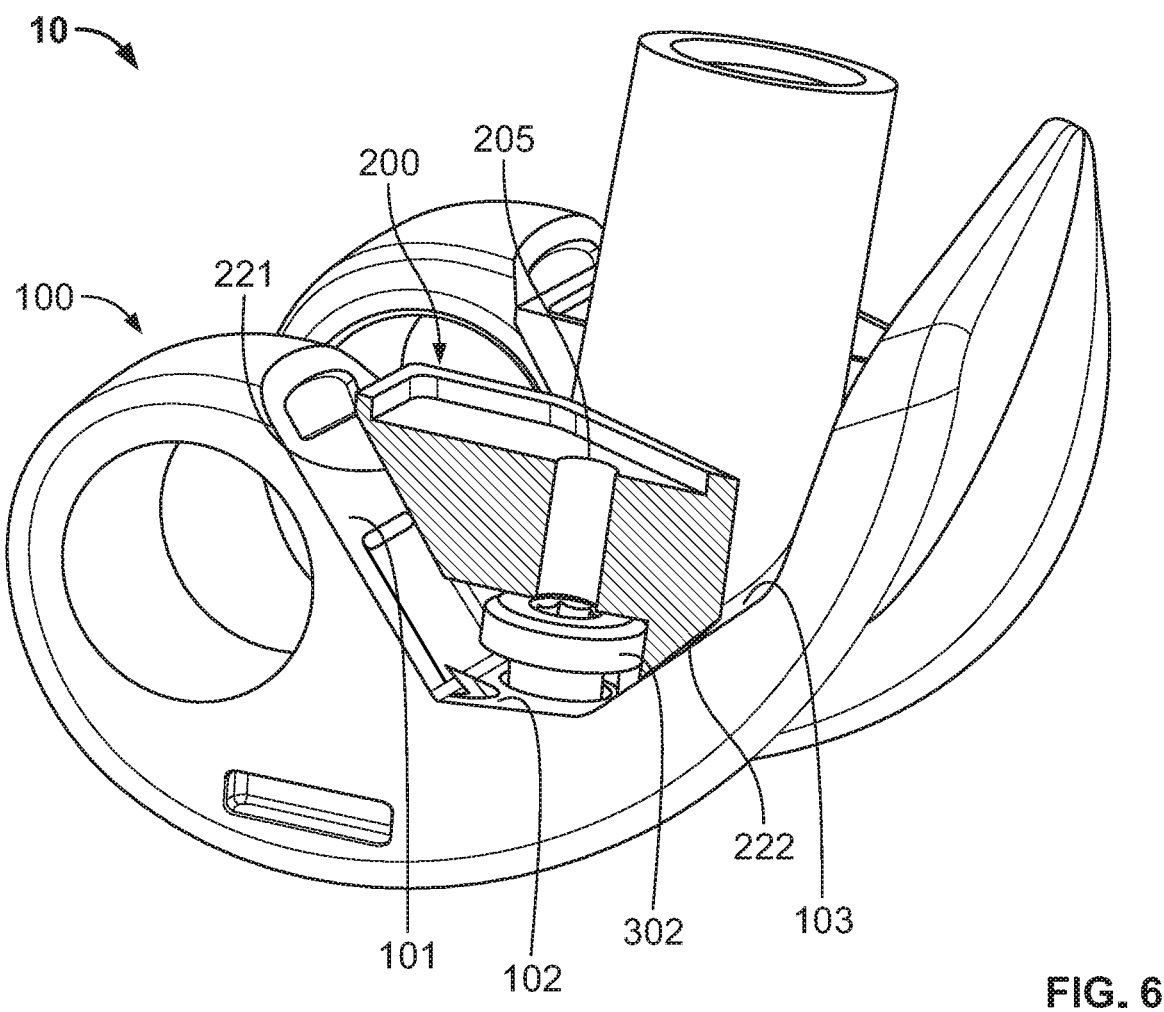
FIG. 6 is a cutaway perspective view of the joint prosthesis system of FIG. 1.

As shown in FIG. 6, when augment 200 is fully engaged to femoral component 100, proximal surface 201 of augment 200 becomes a bone contacting or bone facing surface, particularly for a distal resected surface of a femur. In addition, chamfer surfaces 221 and 222 engage respective first and third inner surfaces 101, 103, distal surface 203 rests on second inner surface 102, and through-bore 205 aligns with aperture 306 such that the entirety of the through-bore 205 extends between the head 302 and proximal end 202 of the augment 200. Moreover, head 302 is positioned between second inner surface 102 and through-bore 205.

In a TKA procedure, if it is found that augment 200 does not adequately compensate for the deficiency, an augment with a larger or lesser thickness may be swapped out with the augment 200 previously connected to femoral component 100. Thus, a first augment 200 may be removed from femoral component 100 and a second, larger, augment 200 may be connected to femoral component. This process may be repeated with various other augments of different thicknesses until a proper fit is determined. To facilitate this process surgeon is provided with a kit of a plurality of augments 200 of different sizes as well as femoral component 100. In addition, it should be understood that where a resected bone surface does not require augmentation, no augment may be provided on that side of the bone and femoral component 100. However, some femoral component embodiments contemplated but not shown may require an augment 200 of nominal zero thickness for a non-deficient bone surface.

While the foregoing description describes a femoral component and an augment for connection thereto, it is should be understood that the foregoing can be applied to other joint replacement components and augments for augmenting the same. For example, it is contemplated that a tibial augment may have a similar slot and through-bore configuration for connection to a baseplate of a tibial component.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic system comprising:
    an augment having a proximal surface and a distal surface, a recessed slot extending along the distal surface, and a through-bore extending between the proximal and distal surfaces and intersecting the recessed slot, the recessed slot being defined at least by opposing rails and a pair of walls of the augment, the walls being separated from each other by a distance greater than a distance separating the rails;
    a coupling component having a head and a body, the head having an aperture and being configured to be slidingly received onto the rails and between the walls within the recessed slot wherein, when the head is received within the recessed slot, the aperture aligns with the through-bore and the body extends between the rails and from the recess; and
    a femoral prosthesis having an articular side defining condylar portions and a bone facing side opposite the articular side, the bone facing side defining a coupling bore, the coupling bore being configured to receive the body of the coupling component for connection thereto.

2. The orthopedic system of claim 1, wherein the augment includes a plurality of side surfaces extending between the proximal surface and the distal surface, and the recessed slot extends through the distal surface and through a first side surface of the plurality of side surfaces.

3. The orthopedic system of claim 1, wherein the coupling component is a threaded fastener and the body of the coupling component is a threaded shaft.

4. The orthopedic system of claim 1, wherein the through-bore has a diameter smaller than a cross-sectional dimension of the head.

5. The orthopedic system of claim 1, wherein the augment is monolithic.

6. An orthopedic system comprising:
    an augment having a proximal end and a distal end, a through-bore extending between the proximal end and the distal end, the through-bore being configured for insertion of a tool;
    a fastener having a head and a body, the head having an aperture, the fastener being rotatably connected to the distal end of the augment such that the aperture aligns with the through-bore, the entirety of the through-bore extends between the head and the proximal end of the augment, and the entirety of the fastener, including the head and the body, is positioned distal of the proximal end of the augment; and
    a monolithic femoral prosthesis having an articular side defining condylar portions and a bone-facing side opposite the articular side, the bone-facing side defining an inner surface, the inner surface having a bore configured to receive the body of the fastener such that, when the body of the fastener is received within the bore of the femoral prosthesis, the distal surface of the augment contacts the inner surface of the femoral prosthesis and the head of the fastener is captured between the femoral prosthesis and the augment.

7. The orthopedic system of claim 6, wherein the augment includes a plurality of side surfaces extending between the proximal and distal surfaces.

8. The orthopedic system of claim 7, wherein the distal end of the augment includes a slot configured to slidingly receive the head of the fastener.

9. The orthopedic system of claim 8, wherein the slot is recessed within the augment such that it extends through the distal surface and a first side surface of the plurality of side surfaces.

10. The orthopedic system of claim 8, wherein the slot extends in an anteroposterior direction and is defined by a lateral wall, medial wall, and anterior wall, the lateral and medial walls intersecting the anterior wall such that the anterior wall defines an anterior abutment for the head of the fastener.

11. The orthopedic system of claim 6, wherein the through-bore has a diameter smaller than a cross-sectional dimension of the head.

12. The orthopedic system of claim 6, wherein the femoral component defines a transverse opening extending through the condylar portion and being configured to receive an axle therein.

13. The orthopedic system of claim 6, wherein the fastener is a screw and the body is a threaded shaft.

14. The orthopedic system of claim 6, wherein the through-bore has a smaller cross-sectional dimension than that of the head of the fastener so as to prevent the passage of the head through the through-bore.

15. An orthopedic system comprising:
    an augment having a proximal surface and a distal surface, and defining a recessed slot extending through the distal surface and a through-bore extending through the proximal surface and intersecting the recessed slot, the through-bore being configured for insertion of a tool, the augment further comprising a pair of opposing rails and a pair of opposing walls at least partially defining the slot, each rail being positioned along a respective one of the walls such that the walls are separated by a distance greater than the rails;
    a fastener having a head and a body, the head being configured to be rotatably received within the recessed slot such that the head is captured by the rails and between the walls to prohibit axial movement thereof and such that the aperture aligns with the through-bore; and
    a femoral prosthesis having an articular side defining condylar portions and a bone-facing side opposite the articular side, the bone-facing side defining a first inner surface, the first inner surface having a bore configured to receive the body of the fastener.

16. The orthopedic system of claim 15, wherein the femoral component includes a second inner surface intersecting the first the inner surface, and the augment includes a side surface intersecting the distal surface of the augment, the distal surface and side surface being configured to respectively contact the first and second inner surfaces of the femoral prosthesis when the body of the fastener is received within the bore of the femoral prosthesis.

17. The orthopedic system of claim 15, wherein the recessed slot extends through the distal surface and the side surface.

18. The orthopedic system of claim 15, wherein the through-bore has a diameter smaller than a cross-sectional dimension of the head.

19. The orthopedic system of claim 15, wherein the femoral component defines a transverse opening extending through the condylar portion and being configured to receive an axle therein.

20. The orthopedic system of claim 15, wherein the augment is monolithic.

\* \* \* \* \*